(12) United States Patent
Monstadt et al.

(10) Patent No.: US 11,369,499 B2
(45) Date of Patent: Jun. 28, 2022

(54) INSERTION AND RELEASE SYSTEM FOR IMPLANTS

(71) Applicant: Phenox GmbH, Bochum (DE)

(72) Inventors: Hermann Monstadt, Bochum (DE); Ralf Hannes, Dortmund (DE); Diana Stateczny, Bochum (DE); Stefan Rolla, Bochum (DE); Manuel Salin, Bochum (DE)

(73) Assignee: Phenox GmbH, Bochum (DE)

( * ) Notice: Subject to any disclaimer, the term of this patent is extended or adjusted under 35 U.S.C. 154(b) by 112 days.

(21) Appl. No.: 14/915,695

(22) PCT Filed: Sep. 3, 2014

(86) PCT No.: PCT/EP2014/068691
§ 371 (c)(1),
(2) Date: Mar. 1, 2016

(87) PCT Pub. No.: WO2015/032798
PCT Pub. Date: Mar. 12, 2015

(65) Prior Publication Data
US 2016/0206455 A1    Jul. 21, 2016

(30) Foreign Application Priority Data

Sep. 3, 2013 (DE) .................. 102013014523.6

(51) Int. Cl.
| | |
|---|---|
| *A61F 2/966* | (2013.01) |
| *A61F 2/844* | (2013.01) |
| *A61F 2/90* | (2013.01) |

(52) U.S. Cl.
CPC .............. *A61F 2/966* (2013.01); *A61F 2/844* (2013.01); *A61F 2/90* (2013.01);
(Continued)

(58) Field of Classification Search
CPC .. A61F 2/966; A61F 2/844; A61F 2/90; A61F 2002/9665; A61F 2250/0036; A61F 2250/0037; A61F 2250/0039
See application file for complete search history.

(56) References Cited

U.S. PATENT DOCUMENTS

| | | | | | |
|---|---|---|---|---|---|
| 5,338,296 | A | * | 8/1994 | Dalessandro | ......... A61M 25/01 604/103.05 |
| 5,690,644 | A | * | 11/1997 | Yurek | ........................ A61F 2/95 606/198 |

(Continued)

FOREIGN PATENT DOCUMENTS

| | | |
|---|---|---|
| CN | 103200884 | 7/2013 |
| DE | 102009006180 | 5/2010 |

(Continued)

OTHER PUBLICATIONS

International Search Report of the International Searching Authority with English Translation issued in the corresponding PCT International Application No. PCT/EP2014/068691, dated Dec. 18, 2014 (5 pages).

(Continued)

*Primary Examiner* — Jing Rui Ou
(74) *Attorney, Agent, or Firm* — Crockett & Crockett, PC; K. David Crockett, Esq.

(57) ABSTRACT

The invention relates to a device for the introduction of an implant (1) into blood vessels of the human body, said device comprising an implant (1), a pusher or insertion wire (14), and a tube-like sheathing (13), wherein the implant (1) is capable of being deformed inside a microcatheter in a manner that allows it to assume a shape of reduced diameter and, after omission of such external constraint exerted by the microcatheter, expand at the placement site and adapt to the blood vessel diameter, and wherein the implant (1) being provided at the proximal end with connection elements (6)

(Continued)

attaching it to a retaining element (15) by means of which the implant (1) is coupled to the pusher wire (14), and wherein the retaining element (15) is provided with peripheral cutouts (16) into which the connecting elements (6) are fitted, with the tube-like sheathing (13) being drawn in a form-closed manner over the retaining element (15) with fitted connection elements (6) such that the connection elements (6) are secured within the cutouts (16) of the retaining element (15) and the implant (1) being released by the retraction of the tube-like sheathing (13) in proximal direction, with the outer diameter of the tube-like sheathing (13) varying between the proximal and the distal end. In this manner, high pliability is achieved in some sections of sheathing (13) which is conducive to maneuvering through narrow blood vessels, and, moreover, sufficient tensile strength is available for the purpose of releasing implant (1).

9 Claims, 7 Drawing Sheets

(52) U.S. Cl.
CPC ............... *A61F 2002/9665* (2013.01); *A61F 2250/0036* (2013.01); *A61F 2250/0037* (2013.01); *A61F 2250/0039* (2013.01)

(56) References Cited

U.S. PATENT DOCUMENTS

| | | | | |
|---|---|---|---|---|
| 5,772,669 A * | 6/1998 | Vrba | ........................ | A61F 2/95 606/195 |
| 6,083,257 A * | 7/2000 | Taylor | ...................... | A61F 2/90 623/1.46 |
| 6,488,654 B2 | 12/2002 | Gonzalez et al. | | |
| 8,652,192 B2 * | 2/2014 | St. Germain | ............. | A61F 2/91 623/1.1 |
| 2001/0034549 A1 * | 10/2001 | Bartholf | .................... | A61F 2/95 623/1.12 |
| 2002/0052640 A1 * | 5/2002 | Bigus | ........................ | A61F 2/07 623/1.11 |
| 2002/0055767 A1 * | 5/2002 | Forde | ....................... | A61F 2/01 623/1.11 |
| 2002/0120322 A1 * | 8/2002 | Thompson | ................ | A61F 2/91 623/1.11 |
| 2002/0133171 A1 * | 9/2002 | Que | ..................... | A61B 17/221 606/127 |
| 2004/0153049 A1 * | 8/2004 | Hewitt | .............. | A61M 25/0012 604/527 |
| 2004/0236406 A1 * | 11/2004 | Gregorich | ................. | A61F 2/91 623/1.16 |
| 2005/0004553 A1 * | 1/2005 | Douk | ............... | A61B 17/12022 604/523 |
| 2005/0090890 A1 * | 4/2005 | Wu | ........................... | A61F 2/95 623/1.11 |
| 2005/0113902 A1 | 5/2005 | Geiser et al. | | |
| 2006/0259120 A1 | 11/2006 | Vongphakdy et al. | | |
| 2007/0100422 A1 * | 5/2007 | Shumer | ..................... | A61F 2/95 623/1.11 |
| 2007/0255390 A1 * | 11/2007 | Ducke | ........................ | A61F 2/95 623/1.11 |
| 2009/0088791 A1 * | 4/2009 | Drasler | ................... | A61F 2/013 606/200 |
| 2010/0152834 A1 * | 6/2010 | Hannes | ..................... | A61F 2/90 623/1.15 |
| 2011/0251666 A1 | 10/2011 | Joshua et al. | | |
| 2012/0303111 A1 | 11/2012 | Joshua et al. | | |
| 2013/0211492 A1 | 8/2013 | Schneider et al. | | |

FOREIGN PATENT DOCUMENTS

| | | |
|---|---|---|
| JP | 10503411 | 3/1998 |
| JP | 2011522650 | 8/2011 |
| JP | 2013512705 | 4/2013 |
| JP | 2013521022 | 6/2013 |
| JP | 2013523327 | 6/2013 |
| KR | 20080005963 | 1/2008 |
| WO | WO2006105500 | 10/2006 |
| WO | WO2008107172 | 9/2008 |

OTHER PUBLICATIONS

Written Opinion of the International Search Authority (Form PCT/ISA/237) with English Translation issued in the corresponding PCT International Application No. PCT/EP2014/068691, (14 pages).
International Preliminary Report on Patentability Chapter I issued in the corresponding PCT International Application No. PCT/EP2014/068691, dated Mar. 8, 2016 (7 pages).
Canadian Office Action dated Dec. 15, 2017 from Canadian Patent Application No. 2922882.
Japanese Office Action dated Aug. 7, 2018 from Japanese Patent Application No. 2016-537344.

* cited by examiner

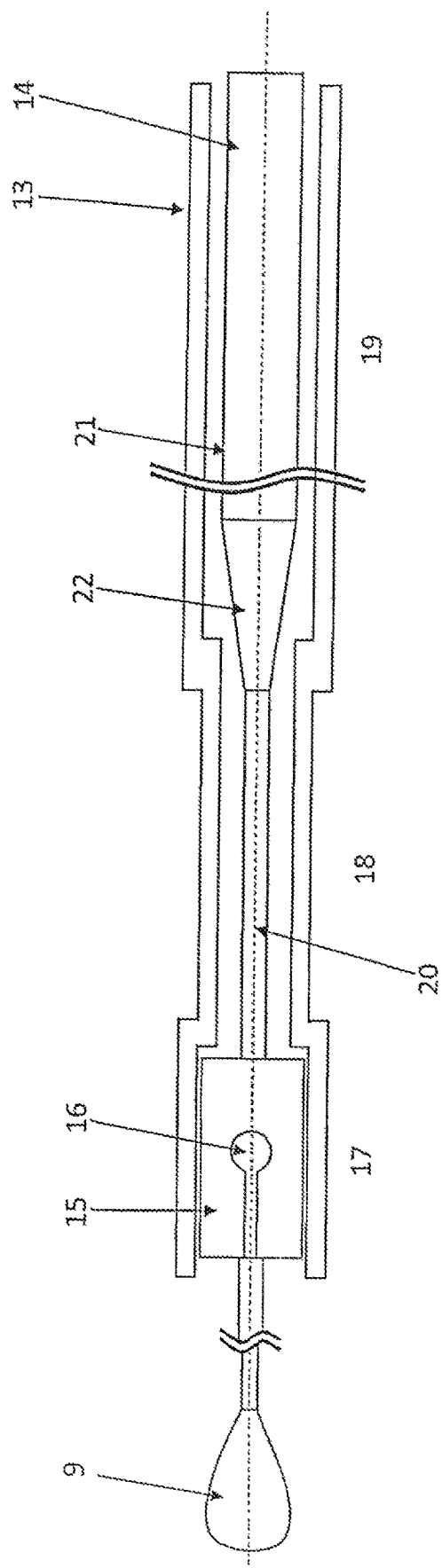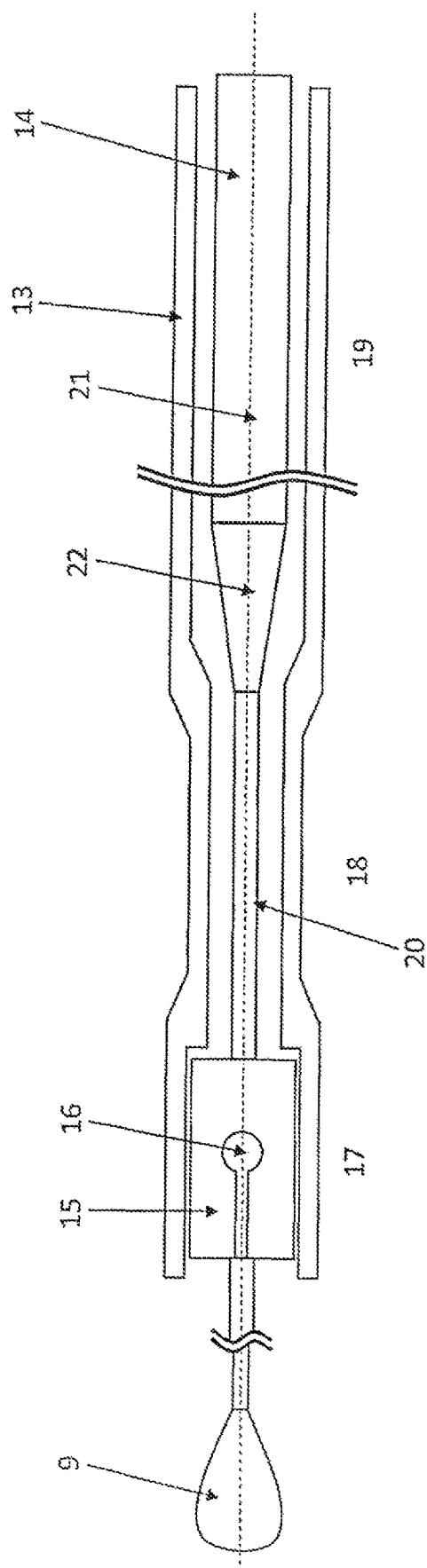

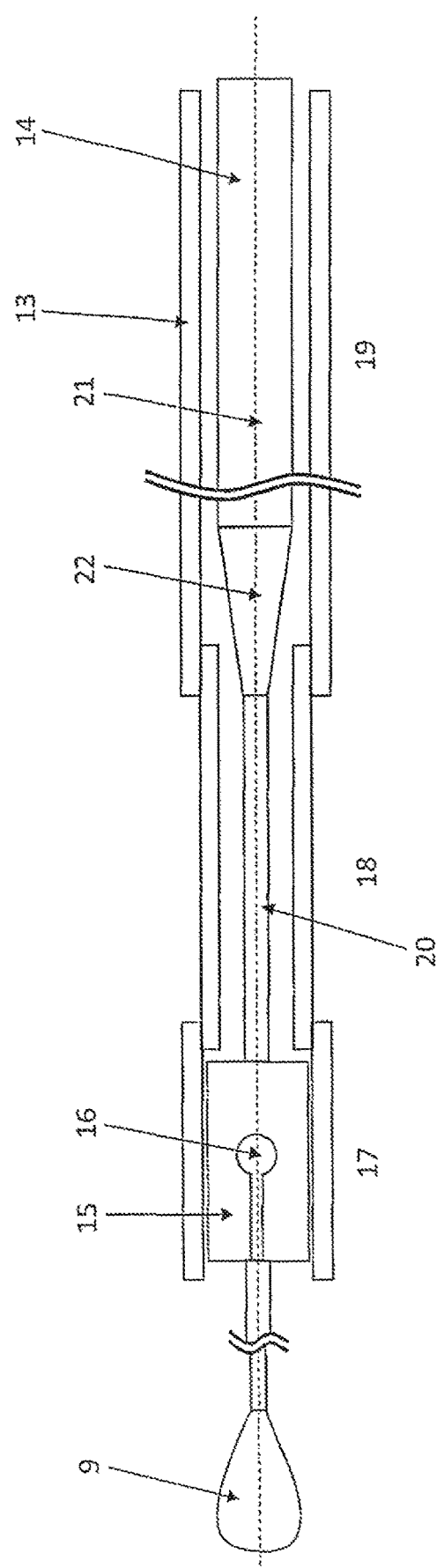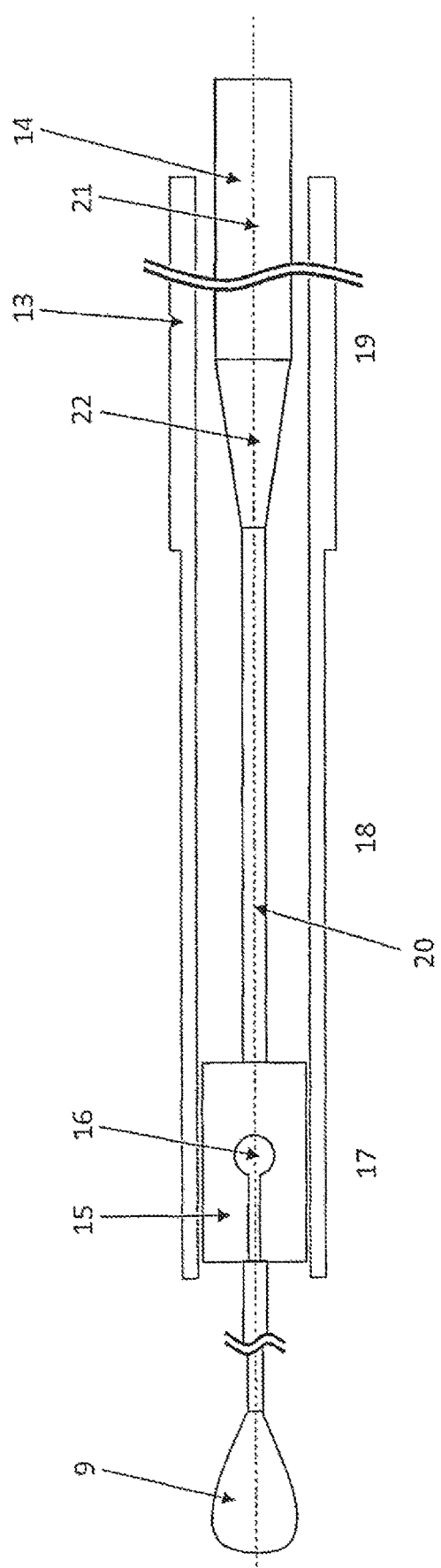

INSERTION AND RELEASE SYSTEM FOR IMPLANTS

The invention relates to a device for the introduction of an implant into blood vessels of the human body, said device comprising an implant, a pusher or insertion wire, and a tube-like sheathing, wherein the implant is capable of being deformed inside a microcatheter in a manner that allows it to assume a shape of reduced diameter and, after omission of such external constraint exerted by the microcatheter, expand at the placement site and adapt to the blood vessel diameter, and wherein the implant being provided at the proximal end with connection elements attaching it to a retaining element by means of which the implant is coupled to the pusher wire, and wherein the retaining element is provided with peripheral cutouts into which the connecting elements are fitted, with the tube-like sheathing being drawn in a form-closed manner over the retaining element with fitted connection elements such that the connection elements are secured within the cutouts of the retaining element and the implant can be released by the retraction of the tube-like sheathing in proximal direction.

Arteriovenous malformation may significantly impair a patient and may even result in fatal risks. In particular, this applies to arteriovenous fistulas and aneurysms, in particular when these are found to exist in the cerebral region. Usually it is attempted to occlude this kind of malformations by means of implants. Such implants are as rule placed by endovascular methods using catheters.

Especially when treating aneurysms implanting platinum spirals has proven its worth, said spirals fill the aneurysm more or less completely, largely obstruct the blood inflow and enable a local thrombus or clot to form which fills and ultimately closes off the aneurysm. Nevertheless, this treatment approach only suits aneurysms that have a relatively narrow access to the vessel system, so-called aciniform aneurysms. In the event of vessel protuberances having a wide access to the blood vessel there is a risk that the implanted spirals may become flushed out and cause damage to other areas of the vascular system.

In such cases it has already been proposed to place into position a kind of stent that "bars" the opening of the aneurysm and in this way prevents the occlusion coils from being flushed out. Stents of this nature that are provided with a wide-meshed wall have certain drawbacks, however.

On the one hand, this concerns the wide-meshed structure which does not prevent blood from entering the aneurysm. So if the occlusion means does not occupy the aneurysm space adequately the pressure exerted on the vessel wall persists unabated. An aftertreatment in this case may be difficult, however, because the stent will obstruct access to the aneurysm and impair the placement of additional occlusion means.

Another drawback is that the stent cannot be adapted to its placement site. In the interest of functioning optimally the stent should have close contact with the vessel wall but not exert excessive pressure on the wall. Other than stents serving the purpose of expanding vessels to counteract stenoses this type of stent must rather be viewed as a kind of sleeve the influence of which on the vessel lumen and endothelium wall of the vessel shall be as slight as possible. It thus follows that this stent type is only of limited use when it comes to meet the respective requirements even if it has been selected especially for the envisaged purpose.

Stents consisting of wire braiding are known for a long time, particularly for applications in the coronary area. These stents are usually manufactured as a round braiding structure with the individual wire filaments forming the stent wall in layers of oppositely running spirally or helically shaped elements. In this way a mesh braiding is produced that both supports in radial direction and is permeable to blood.

Such stents of circular braiding design consisting of filaments are, when used for the treatment of stenoses, more often than not expanded hydraulically by means of balloons at the placement site and attached to the vessel wall. During placement the balloon attached to a pusher wire serves as transportation element onto which the stent is crimp-mounted. However, such a transportation element should not be used for implants intended to influence or channel the flow of blood in the cerebral region; on the contrary, an implant automatically adapting to the vessel diameter and leaning against the vessel wall is of advantage in this case.

Publication WO 2008/107172 A1 describes an implant the braiding of which has an elongated shape of reduced diameter within a microcatheter and expands at the placement site thus adapting to the vessel diameter and increasing its braiding density, wherein the filament ends projecting at the implant ends are brought together at least in pairs and connected with each other. In this manner, an implant was provided that was capable of adapting to the relevant vessel diameter and had atraumatically designed filament ends.

In accordance with this state of the art connecting elements are arranged on the joined filament ends that interact with retaining elements according to the key-and-lock principle. The retaining element via which the implant is coupled to a pusher wire has cutouts accommodating the fittingly designed connecting elements. The connecting elements are provided with thickenings, for example of ball shape, so that they are secured in the cutouts of the retaining element in a form-closed manner. Fixation of the connecting elements in the cutouts can be achieved with the help of a tube drawn in a form-closed manner over the retaining element with connecting elements in place. When the implant has reached its ultimate position this tube or hose is retracted in proximal direction and in this way liberates the implant. Following this, the pusher wire with retaining element, tube and catheter can be withdrawn and extracted from the body For the introduction of such an implant into the blood vessel system it is of advantage when the overall system of the device, especially the pusher wire and tube-like element, is as flexibly designed as possible. This is particularly true for intracranial areas where very small blood vessels exist. In the interest of maximum flexibility a tube could basically be selected that has a low wall thickness and small outer diameter but it has turned out in this case that the tube may expand in longitudinal direction when retracted. This results in the tube movement at one end not being accurately translated to the other end of the tube. As a consequence, the connecting element may not be released as desired from the retaining element because the distal end of the tube still covers the cutouts of the retaining element in spite of the fact that a force is exerted at the proximal end.

It is therefore the objective of the invention to provide an implant of the kind first mentioned above that on the one hand yields sufficient flexibility to be guided also through narrow-lumened blood vessels, respectively a microcatheter of small inner diameter and on the other enables the implant to be released without difficulty when the tube is retracted.

As proposed by the present invention this objective is accomplished by a device for the introduction of an implant into blood vessels of the human body, said device comprising an implant, a pusher or insertion wire, and a tube-like sheathing, wherein the implant is capable of being deformed inside a microcatheter in a manner that allows it to assume a shape of reduced diameter and, after omission of such external constraint exerted by the microcatheter, expand at the placement site and adapt to the blood vessel diameter, and wherein the implant being provided at the proximal end with connection elements attaching it to a retaining element by means of which the implant is coupled to the pusher wire, and wherein the retaining element is provided with peripheral cutouts into which the connecting elements are fitted, with the tube-like sheathing being drawn in a form-closed manner over the retaining element with fitted connection elements such that the connection elements are secured within the cutouts of the retaining element and the implant can be released by the retraction of the tube-like sheathing in proximal direction, with the outer diameter of the tube-like sheathing varying between the proximal and the distal end.

Varying the outer diameter of the tube-like sheathing between the proximal and the distal end makes it possible to advantageously combine high flexibility with a problem-free and predictable release capability. In certain sections of the sheathing, especially in an area proximally adjacent to the distal section that directly enwraps the retaining element, high flexibility is of great significance to enable the entire device when inserted to also follow smaller-sized vessel convolutions. For this reason, a small outer diameter is regarded expedient here. On the other hand, the segments of the tube-like sheathing located further in proximal direction should offer adequate resistance to avoid undesirable elongation. In the proximal segment this is an essential requirement to be met as this section constitutes the major part of the overall length of the sheathing making it necessary that its stretchability in longitudinal direction is kept to a minimum, otherwise the total elongation over the entire sheathing length may be undesirably high. In the distal segment covering the retaining element increased resistance against an undesirable elongation may be of advantage as well to make sure this segment of the sheathing actually moves proximally during retraction and does not just stretch in longitudinal direction. For that reason, the distal section as well may have an outer diameter that is greater than that of the middle section but this is not of absolute necessity. The desirable outer and inner diameter in the distal section also depends on the dimensions of the enwrapped retaining element.

For placement the implant is first moved forward through the microcatheter to the desired position by means of the pusher wire. The connecting elements secured within the cutouts of the retaining element are located at the proximal end of the implant that is thus enwrapped by the tube-like sheathing which also is true for the retaining element itself and often the entire pusher wire. When it is intended to release the implant the microcatheter is retracted initially. However, this alone does not result in a complete detachment because the tube-like sheathing of the retaining element continues to hold in place the connecting elements located in the cutouts of the retaining element. The cutouts are located in the outer zone of the retaining element; due to the expansion of the implant having been detached from the microcatheter there is a natural tendency for the connecting elements to move outwards and in this way disengage from the cutouts. However, this cannot be achieved before the tube-like sheathing has been pulled back. Therefore, even after the microcatheter has been drawn back there is still sufficient time available for the attending physician to analyze the prevailing situation and then decide whether to finalize the detachment of the implant by retracting the sheathing in proximal direction or, if the placement of the implant is not as desired, move the implant back into the microcatheter by pulling back the pusher wire and place it in position at another site, or if thought expedient remove the device altogether from the patient's body. As soon as the correctly placed implant has been successfully detached the pusher wire together with the retaining element as well as the tube-like sheathing can be retracted into the microcatheter and together with it removed from the blood vessel system.

In the framework of the description the term proximal shall be understood to be situated nearest to the attending physician, meaning the proximal end points into the direction external to the body. Vice versa, the distal end faces away from the physician, i.e. points towards the inside of the body.

Typically, the tube-like sheathing extends in proximal direction from the retaining element whose cutouts must be covered to enable the connecting element to be safely secured within the cutouts to the outside of the body. It is, however, also conceivable for the sheathing to not enwrap the entire pusher wire, with the sheathing just covering the retaining element being sufficient. In this case the sheathing is retracted via a second wire or thread running from the sheathing in proximal direction parallelly to the pusher wire.

Accordingly, a tube-like sheathing is considered advantageous that comprises a distal section covering inter alia the retaining element, an adjacently arranged middle section of small outer diameter extending in proximal direction, and a proximal section of large outer diameter arranged adjacent to the middle section and extending in proximal direction. Moreover, it may be expedient for the distal section to have a large outer diameter so as to enwrap the retaining element with the connecting elements securely in place. In other words, the section covering the cutouts in the retaining element has a larger outer diameter and thus higher stiffness than the middle section adjoiningly arranged in proximal direction whose flexibility being of special significance for the introduction of the device. The by far longest section which is denoted here as proximal section has a large outer diameter to enable the sheathing to be introduced and retracted over longer distances as well.

Typically, the length of the middle section ranges between 50 and 500 mm, in particular between 80 and 120 mm, and especially preferred is approximately 100 mm. The distal section may, for example, have a length of between 2 and 10 mm; this will usually be sufficient to cover the cutouts in the retaining element. The total length of the sheathing may amount to between 1000 and 2000 mm, e.g. 1800 mm, with the proximal section normally being the longest having a length ranging between 500 and 1900 mm.

In the context of the invention the terms "large outer diameter" and "small outer diameter" shall be understood such that in areas where a large outer diameter exists the outer diameter is greater than in areas where a small outer diameter has been arranged. The exact dimensions may vary same as the proportional relation of the diameters, in particular depending on the conditions prevailing in the blood vessel system and the specific application. Typically, a large outer diameter ranges between 0.4 and 0.8 mm, in particular between 0.5 and 0.7 mm, for example amounts to approx. 0.6 mm. A typical small outer diameter is in the range of between 0.3 and 0.55 mm, in particular between 0.4 and 0.5 mm, for example amounts to approx. 0.45 mm.

Adjoining the proximal section of the tube-like sheathing usually having a large outer diameter a proximal end may also be arranged that again has a relatively small outer diameter. In this case, the tube-like sheathing is expediently clamped onto the pusher wire, for example by using a torquer, so as to produce a frictional connection and in this way rule out any undesirable mutual displacement between pusher wire and sheathing. During the application of the inventive implant a displacement may not occur before the implant has been released.

To facilitate the retraction of the tube-like sheathing with a view to liberating the implant a gripping means can be arranged at the proximal end of the sheathing independently of the outer diameter prevailing in this area. This can be provided in the form of a thickening element or as a sleeve surrounding the proximal end of the sheathing. If the implant is about to be released the torquer clamping the sheathing onto the pusher wire is as a rule slackened and, if thought expedient, newly clamped on the pusher wire with a view to improving the grip on the wire.

Following this, the user can now take hold of the sheathing via the gripping means and pull it back in proximal direction.

The passage of the implant including pusher wire and surrounding tube-like sheathing through the catheter can be facilitated in such a way that the outside of the tube-like sheathing is provided with a coating that reduces the friction between sheathing and catheter. Preferably, this coating is of hydrophilic nature.

As regards the retraction of the tube-like sheathing it is also considered meaningful to keep the frictional forces arising between pusher wire and sheathing to a minimum. For this purpose and at least in partial areas a friction-abating coating may be applied to the outside of the pusher wire, respectively inside of the tube-like sheathing. Preferred is the use of polytetrafluoroethylene (PTFE). This applies particularly to areas where the pusher wire has been sanded back which is typically true for the proximal end so as to enable seizure by means of a torquer.

As per a preferred embodiment of the invention not only the outer diameter varies but also the wall thickness of the tube-like sheathing, i.e. in large diameter areas the sheathing has a greater wall thickness than in areas where a small diameter is provided. Reducing the wall thickness will result in even higher flexibility and pliability of the sheathing so that inside the microcatheter it can easily follow even fine ramifications of the blood vessel system.

As per an especially preferred embodiment the tube-like sheathing is produced on the basis of a uniformly structured sheathing having at least throughout the major portion of its length a constant outer and inner diameter and a constant wall thickness as well. From this sheathing and in the desired sections of it material is removed on the outside which results in the outer diameter to be reduced. Since no material is removed from the sheathing interior the wall thickness of it will decrease to the same extent. In this way, a tube-like sheathing is obtained that is of one-piece design comprising partial sections, particularly the middle section, where the outer diameter as well as the wall thickness have been reduced by material removal. In other partial sections, for example in the proximal and, as the case may be, distal sections, material will as a rule not be removed so that the original outer diameter is maintained in these areas.

The removal of material may basically be carried out by processes known in the prior art, for example by turning, grinding or shaving making use of mechanical tools or with the aid of laser techniques. Material may also be removed at the proximal end so as to enable a torquer to be properly mounted here.

Typically, the tube-like sheathing is made of plastic material. For this purpose, polyimides have turned out to be of special worth. However, other materials may be employed here as well, for example polypropylene or polytetrafluoroethylene (PTFE). Combinations of different plastic materials or multilayered, coextruded polymers may also be used. Moreover, the tube-like sheathing may be provided with additional reinforcing measures by embedding fibers into the sheathing, for example metal fibers. Conceivable in this case is, for example, a tube-like sheathing reinforced by a fabric or braiding.

Aside from this, the tube-like sheathing may also be made of metal, however it should have a thin-walled design to avoid its bending stiffness to be undesirably high. As metal in this case nickel-titanium alloys such as nitinol may in particular be employed.

To enable the bending stiffness to be further reduced the tube-like sheathing may be provided with recesses or thinner material portions, for example in the form of slits or openings. This applies irrespective of the material used for the tube-like sheathing, i.e. both for plastic materials and for metals. These recesses/thinner material portions may be arranged especially in certain zones of the tube-like sheathing where a low bending stiffness is of great significance, for example in the distal area, but may also be provided over the entire length of the tube-like sheathing. In this manner, the flexibility of the sheathing is increased without the tensile strength of the sheathing being influenced negatively.

The removal of material may take place in such a way that the tube-like sheathing has a plurality of different outer diameters when the removal process has been concluded. In particular, there may be a gradual transition between sections of large outer diameter and those of small outer diameter and vice versa, for example by providing several small steps resulting in the different outer diameters to vary just slightly. Likewise, a continuous transition may be arranged for so that the outer diameter reduces or increases in a uniform manner. In this case the transition is of tapered design. When viewed as a longitudinal section, the sheathing wall at locations where the outer diameter transitions from large to small may be provided in the form of a bevel, an inclination or have a round or bow-shaped configuration.

Alternatively, the tube-like sheathing may also consist of a plurality of individual parts. In this case, the partial sections of the sheathing of different outer sections are attached to each other, usually by a bonding or fusing method. Expediently, the partial sections can be attached to each other by using adhesives.

When joining the partial sections of different outer diameters said sections should overlap to ensure the connections are safely made, in particular the bonding surface should be adequately sized for the adhesive bond. If thought expedient, the inner diameter of a partial section of greater outer diameter can be widened to enable a partial section of smaller diameter to be partially inserted. Additionally, steps can be taken to ensure the transition between the partial sections extends as uniformly as possible and arrange for each outer diameter to be increased or reduced gradually and not abruptly or step-like. For this purpose the partial sections can be chamfered, however the material may also be removed in another way. Optionally, a certain additional amount of a suitable material, for example an adhesive, can be applied and in this way bring about a continuous transitional passage from a large to a small outer diameter.

Moreover, the partial sections may also overlap over longer distances, for instance one layer of the tube-like sheathing may run continuously over the major part of the length of the tube-like sheathing. A layer may be arranged that starts at the distal end or slightly proximal of the distal end of the sheathing and extends without interruption up to the proximal end of the sheathing which enables the sheathing inner diameter to be kept largely uniform in this manner. A uniform inner diameter offers manufacturing advantages. In certain sections, especially in the distal and proximal section, an outer sheathing layer is applied to the outside of the continuous layer of the sheathing. The inner and outer layers are bonded together, in particular by adhesive methods. In places where the inner and outer layers are bonded together a sheathing of greater outer diameter and greater total wall thickness is produced in this way, whereas in sections where no outer layer exists the outer diameter and the wall thickness are smaller. Surprisingly, it has been found in this context that a multi-layer design gives more flexibility also to those sections of the sheathing that have a large outer diameter, which is particularly true for the proximal section. As a result of the relatively great wall thickness and associated large cross-sectional area of the outer wall the tensile strength, however, is high. In comparison with a single-layer structure of the sheathing wall having an identical overall wall thickness, the flexibility will thus be higher while the tensile strength is of comparable magnitude.

With this embodiment as well the transitions between sections of large and small outer diameter may of course be of continuous configuration or provided in the form of several small steps. Aside from this and in addition to the inner and outer layer, the tube-like sheathing may be provided with further layers which means the sheathing may basically be formed of an optional number of layers.

Irrespective of the specific design of the inventive sheathing the clearance between the pusher wire and the inner sheathing wall is of significance insofar as if there is too great a clearance when feeding in the microcatheter takes place bending or folding over may occur in the event the pusher wire is too thin in relation to the sheathing's inner diameter so that in the worst case any further forward movement is rendered impossible. On the other hand, any insufficient clearance between the inner wall of the sheathing and the pusher wire causes problems insofar as high frictional forces will arise when relative movement occurs that, for instance, may impede the retraction of the sheathing when it is intended to release the implant.

It is considered to be of advantage if an inner layer of the tube-like sheathing extends at least to a large extent continuously from distal to proximal. This means, the inner layer extends over at least 70%, preferably at least 80%, and especially preferred at least 90% of the length. The definition inner layer in this context does not only refer to a layer that initially is provided separately and subsequently bonded to an outer layer but also to the inner part of a sheathing of one-piece design as it has been described hereinbefore. In this way, not only a uniform inner sheathing diameter is achieved but undesirable elongation or stretching of the sheathing during retraction in proximal direction will also be avoided to a great extent. On the one hand, sections where flexibility is of considerable significance, in particular in the middle section, are designed to be especially thin and resilient so that the sheathing can be well navigated through narrow blood vessels. On the other hand, further sections, in particular the proximal and, as the case may be, the distal section, offer sufficient resistance to counteract an undesirable elongation of the sheathing in the event it is withdrawn in proximal direction. In this manner, the implant can be released safely and without difficulty.

Also the diameter of the pusher wire may vary for the respective sections. In particular, the diameter may distally be smaller than in the proximal section because a low bending stiffness of the pusher wire is also of advantage distally to enable it to follow within the microcatheter the configuration of the blood vessel as easily as possible. However, if the diameter is too small this may also lead to the pusher wire being bent when moved forward resulting in any feed motion to be impeded or even rendered impossible. It is therefore considered expedient for the pusher wire to be of smaller diameter in the distal section because especially in this zone the wire must carefully navigate through the blood vessel configuration whereas in the proximal section the undisturbed feed movement is of prime importance. The diameter may as well vary several times over the length of the pusher wire wherein it preferably increases or decreases uniformly in the transition zones. Therefore, the transitions are preferably of tapered design. Varying the pusher wire diameter may also take place independently of a variation of the outer diameter of the tube-like sheathing; accordingly, the invention also relates to a device as explained by the preamble of claim 1 providing for the diameter of the pusher wire to vary between the proximal end and the distal end.

Even if a small diameter is basically viewed as beneficial in the distal section of the pusher wire, individual areas of the pusher wire may again be of greater diameter in the distal section. This applies especially to the tip of the pusher wire. However, when dividing the pusher wire into a proximal and a distal half it is considered to be expedient if, on average, the diameter in the distal half is smaller than in the proximal half.

The areas of the pusher wire having a small diameter may be enwrapped in polymeric material, for example PTFE. This enables clearance between pusher wire and tube-like sheathing to be avoided preventing any undesirable deformation of the pusher wire during forward movement. Nonetheless, the pusher wire in this section maintains sufficient flexibility and pliability since the stiffness of the wire will hardly be increased by the polymeric material. The polymer may also be applied in the form of a spiral-shaped coil embracing the pusher wire wholly or in partial areas only. Said spiral-shaped coil may also consist of another material, particularly metal.

It is considered advantageous for the outer diameter of the tube-like sheathing and the diameter of the pusher wire to increase or decrease essentially in synchrony with one another. This is also viewed expedient as high flexibility is desirable in identical sections of sheathing on the one hand and pusher wire on the other. Moreover, it is ensured in this manner that the clearance between inner wall of the sheathing and pusher wire remains relatively constant. The diameter of the pusher wire may even considerably decrease distally so that the inner diameter of the sheathing may also be small in the respective sections; for example, it is thus conceivable that in the middle section the sheathing inner diameter is smaller than that of the pusher wire in the proximal section.

The pusher wire may not only extend through the tube-like sheathing but even beyond it through the implant itself which is intended to be released. The pusher wire may, in particular, extend in distal direction even beyond the distal end of the implant when the implant is in compressed state, i.e. is attached to the retaining element. In other words, the pusher wire tip is situated further distally than the distal end of the implant as long as this has not been detached from the retaining element. It is ensured in this way that even when the implant has been liberated an object still extends through the interior of the implant until the pusher wire is retracted. This makes it possible to probe the vessel respectively implant again, for example by passing a catheter over the pusher wire and over the adjoining pusher wire tip. The catheter is moved in this way through the liberated and expanded implant. Only when the pusher wire is finally retracted will the pusher wire tip be removed.

The pusher wire tip may be designed so as to be rotationally symmetric. Its cross section may be round, oval, rectangular or have another basically optional form. It is moreover considered expedient to visualize the pusher wire tip, for example by manufacturing the pusher wire tip itself at least to some extent of a radiopaque material and/or by providing the pusher wire tip with a radiopaque marker arranged at the tip's distal end. The pusher wire tip may be manufactured of stainless steel, nitinol, platinum, platinum/iridium or other metals.

The pusher wire tip and the pusher wire proper may be of one-piece design, in which case the wire in fact has a continuous form. However, the pusher wire tip and the pusher wire may as well be separately manufactured and only connected with each other subsequently. In this case, beneficial characteristics of different materials may be combined with each other, for example the pusher wire itself may be made of stainless steel warranting ease of forward movement while the pusher wire tip may be of a nickel-titanium alloy such as nitinol offering increased flexibility.

The term pusher wire is to be understood broadly and must not always refer to a wire within the conventional sense of the word. For example, other elongated insertion aids having a hollow inner space may be employed as well. In such a case, the above discussed pusher wire diameter corresponds with the outer diameter. It is nevertheless of importance that the pusher wire extends proximally sufficiently for the attending physician to be able to seize and move the wire.

The implant intended to be released preferably has a wall structure comprising individual filaments intersecting with each other and forming a tubular braiding or mesh. The tubular braiding is in most cases of round shape and has a circular cross section when facing its proximal or distal end. However, the braid may also have a shape other than circular, for example an oval cross section may be provided.

As filaments forming the braiding structure individual wires made of metal may be employed but it is also possible to provide strands, i.e. several wires of small diameter arranged so as to form a filament, preferably twisted around each other.

The implant is described hereinafter based on a flow diverter which is suitably employed to influence the blood flow in a vessel in such a manner that arteriovenous malformations are sealed off from the blood flow to the extent possible. The malformations in this context are usually aneurysms. However, use of the inventive device shall not be limited in this respect and the device is basically suitable for other implant types as well which are meant to be inserted into blood vessels and released there, for example traditional stents intended to have a supporting function. The inventive device offers special advantages in conjunction with implants that proximally do not only have a single but several ends which is primarily the case with implants designed in the form of a mesh or braided structure consisting of filaments joined with a view to forming a plurality of proximal ends. These ends of an implant should be released simultaneously which is achievable without difficulty by way of the present invention.

The implant may also serve the purpose of occluding vessels which are to be separated from the blood circulation system, e.g. because they feed blood to tumors. By appropriately selecting the implant diameter to suit the respective vessel diameter the implant should be capable of adapting to the relevant vessel diameter. In the area of enlargements and protuberances it shall expand to its maximum nominal diameter, i.e. the diameter the implant takes up in the absence of any external constraint.

Placement of the implant should be effected in an atraumatic manner without a balloon being used. Via its connecting elements the retaining element reliably secures the implant until the same has finally been released from the microcatheter and until the tube-like sheathing has been retracted and in this way also enables the implant to be drawn back into the microcatheter as long as the liberation has not yet been completed.

Suitable materials for the implant are, in particular, those that have a high restoring force or spring action. These are especially materials having superelastic or shape-memory properties, for example nitinol. To form the individual filaments wires of different diameter may also be used. Such a design makes it possible to combine or counterbalance the advantages and drawbacks associated with wires of different cross sections. In most cases the wire cross section is round but wires having oval or square cross sections or combinations thereof may also be employed.

In any case, it is essential that the implant, on the one hand, is capable of assuming a compressed form so that it can pass through the microcatheter and, on the other, expanding automatically when released from the external force exerted by the microcatheter and then leaning against the inner wall of the vessel at the placement site. The implant can also be manufactured from composite materials, for example using nickel-titanium wires coated with platinum or platinum-wires coated with nickel-titanium. This enables the shape-memory properties of the nickel-titanium alloy (nitinol) to be combined with the radiopacity of platinum.

The diameter of the implant in expanded state typically ranges between 2.5 and 5.0 mm with its length for example amounting to between 20 and 40 mm.

The pusher wire may be manufactured of stainless steel or of a shape-memory material, in particular of a nickel-titanium alloy such as nitinol. In the event of pusher wires the diameters of which vary the pusher wire may be ground to the desired size from a single wire, i.e. material can be removed in areas of smaller diameter. Another option is to join several individual wires with a view to forming a pusher wire at the locations where the diameter of the pusher wire shall be varied. Different materials may be employed in this context. In particular, a pusher wire made of stainless steel may be provided at the distal end with a tip consisting of a nickel-titanium alloy.

In the event the implant serves as a flow diverter it must not necessarily fulfil a supporting function as is the case with common stents. The implant in this case rather serves to channelize the flow of blood in the area of malformations in the sense of a kind of internal sleeve. For example, it shall also prevent occlusion means placed in an aneurysm from being flushed out into the vascular pathway. Moreover, the inflow and/or outflow of blood in an aneurysm can be prevented.

The implants according to the invention are manufactured as braiding consisting of a multitude of filaments, wherein the braid basically forms an endless hose. This endless hose can then be cut to the length desired for the relevant implant. The individual filaments are wound spirally or in the form of a helix, with the individual filaments being intertwined to form a braiding, i.e. crossing one below and above the other. For this purpose, the individual filaments are as a rule wound in two directions thus crossing each other at a constant angle, with this angle of intersection being, for example, 90°. In normal stress-free condition angles of more than 90° are preferable, especially those ranging between 90 and 160°, and the angles meant here are those which are open towards the axial ends of the implant. Provided it is sufficiently dense, such a steep winding of the individual filaments can produce a braiding of high surface density capable of being stretched in axial direction thus yielding significantly smaller diameters. If the stretching forces are omitted and the restoring force of the filament material is sufficiently high the braiding again approaches its nominal diameter, i.e. the originally existing stress-free condition, and expands which at the placement site leads to a close contact with the vessel wall and causes the mesh structure at the wall to become denser. This also applies particularly to areas where vessel enlargements exist. In addition, the surface density of the braid can also be varied by the braiding technique used. In the middle area for example where aneurysms are typically closed off the braided structure of the implant may be denser than in its end regions which ensures the neck of the aneurysm is covered to a great extent. On the other hand, if the surface density in the end regions is reduced this will yield adequate flexibility. Vessel branches (bifurcations) can be taken into account with the implants, for example, by providing areas of lower mesh density. Typically, the filament thickness amounts to 0.01 to 0.2 mm, in particular ranges between 0.02 and 0.05 mm.

In the braid the filament ends protruding from the ends of the implant are joined at least in pairs and connected with each other permanently. This may, for example, be achieved by welding or by a mechanical clasping method, twisting, soldering, or adhesive bonding. A connection of the filament ends may also be achieved by means of a mounted sleeve. Such a sleeve may be attached to the filament ends by a substance-to-substance bond, for example it may be connected by welding or also by crimping. As an alternative the sleeve may be suits ably sized such that thicker slubs or nubs arranged at the ends of the filaments are prevented from passing or sliding through said sleeve. The sleeve is thus slidable in axial direction relative to the filaments but cannot be completely pulled off. It is moreover considered advantageous if the sleeves are of staggered arrangement in axial direction. Such an arrangement will ensure that the sleeves are not positioned one over the other when the implant is compressed so that a smaller overall implant diameter can be achieved.

Joining and connecting the filament ends is of importance, in particular at the proximal end of the implant; experience has shown that even free filament ends do not cause problems at the distal end of the implant. By joining the filament ends at the proximal end connecting elements may as well be created which are suitably secured within the retaining element of the pusher wire. However, it is nonetheless possible to bring together and connect the filament ends with each other also at the distal end of the implant.

Also conceivable is to bring the filament ends together to form first braiding ends which in turn are joined to form second braiding ends, as has been described in DE 10 2009 006 180 A1.

During this process or additionally the joined filament ends may be formed such that they do not cause traumatic effects. In particular, the filament ends may be provided distally and/or proximally with a thicker atraumatic element of roughly spherical or ball shape for example. Such slubs/thickenings may be shaped out of the filament end or attached to it by laser welding, brazing, adhesive bonding, crimping or similar methods.

The slubs/thickenings may at the same time function as connecting elements that fit into the cutouts of the retaining element and are secured therein in a form-closing manner. The connecting elements are arranged at the proximal end of the implant where they serve the purpose of establishing the connection with the pusher wire via the retaining element.

The connecting elements may be formed in a manner that produces and arrange for thickenings of defined diameter at the proximal end of the implant, and said thickenings can be created by fusing with the help of a laser. The slubs/thickenings may be of spherical, oval, rectangular, square or similar shape.

Extensions may also be arranged at the proximal ends of the filaments, with said extensions extending further in proximal direction and having ends provided with said connecting elements. Such an extension element may, for example, consist of a wire arranged at the linkage point of two or more filament ends and further extends in axial direction.

Other than a ball shape the design of the connecting elements may also provide for shapes such as anchors, rectangles or other form pieces. The connecting elements function according to the key/lock principle, i.e. they interact with a retaining element being provided on its periphery with suitable recesses or receptacles. As long as the retaining element and the implant attached to it are moved along within a microcatheter in elongated and diameter-reduced form both are forcibly kept together due to the restraint of the catheter wall; and when the retaining element has exited the microcatheter and the tube-like sheathing has been drawn back in proximal direction the implant expands until it reaches its ultimate diameter and in this way disengages itself from the receptacles provided in the retaining element. The retaining element is usually of rotationally symmetric design and may, for example, be manufactured of stainless steel or nitinol.

However, other embodiments are conceivable as well that are provided with additional connecting elements arranged at the distal end of the implant which are secured by another retaining element. A suitably designed object with two retaining elements may have both retaining elements connected to one and the same pusher wire at a defined distance so that it is ensured the implant of a given length also undergoes a defined elongation and tensioning. In this manner any excessive elongation is ruled out and the restoring forces that are exerted after the implant is liberated within the vessel can be fully effective. As an alternative, the retaining elements may also be attached to two separate pusher wires enabling the implant to be adjusted or elongated by the attending physician or by means of a suitably designed fixation device. The connecting elements located in the retaining element arranged further proximally are only disengaged when the tube-like sheathing has been retracted in proximal direction whereas the connecting elements located in the retaining element arranged further distally are also disengaged either by retracting the sheathing or already upon release from the microcatheter.

In actual practice placement of the inventive implants will be under radiographic control. The implant and, as the case may be, the pusher wire as well should therefore be provided with a radiopaque marker material or entirely consist of a radiopaque material. Such radiopaque materials are in particular tantalum, gold, tungsten, and platinum metals, for example Pt—Ir alloys, with the latter to be given preference. These markers may, for instance, be attached as marker elements to the ends of the filaments in a manner known per se or plaited into the braid structure of the implant as marker filaments. Individual filaments may as well be sheathed in a helix or enclosed in wire consisting of radiopaque material such as platinum. The helix or wire may be attached to the filaments by welding, adhesive bonding or the like. It is also possible to coat or fill the filaments with a radiopaque material.

Radiopaque markers in the form of sleeves surrounding the joined filaments may also be employed. These sleeves may be welded to or crimped onto the ends of the filaments. The radiopaque sleeves may be identical to the sleeves bringing the filament ends together as mentioned hereinbefore and thus fulfill a dual function. The connecting elements as well can be manufactured of a radiopaque material. Moreover, a distal section of the pusher wire may be provided with a helix/coil consisting of a radiopaque material, for example a Pt helix/coil. This is preferably located at a point proximally contiguous to the retaining element.

It is also conceivable to introduce radiopaque substances into the tube-like sheathing. These may be radiopaque particles as they are customarily employed as contrast medium for radiotechnological purposes. Such radiopaque substances are, for example, heavy metal salts such as barium sulfate or iodine compounds. A radiopaque sheathing proves beneficial during implant placement and for localization purposes and may be used either additionally to or instead of marker elements.

Basically, the braiding may be plaited in any known way. It may have a one-plaited and/or multi-plaited structure. Especially when used in a narrowly plaited arrangement a dense braiding will cause the individual filaments to be highly stressed. However, while a multi-plaited design is conducive to removing stresses from the braid, a too highly plaited arrangement on the other hand will cause the bond in the braid to deteriorate. The plaiting method indicates how many times a given filament passes crossing filaments on the same side of such filaments before it changes sides and subsequently passes on the other side of a corresponding number of crossing filaments. In case of a two-plaited arrangement a filament, for example, passes in succession over two crossing filaments and then in succession along the underside of two crossing filaments.

In particular, also multi-ply filaments may employed. The plying indicates the number of joined, parallelly arranged individual filaments. Single or multiple plying may be provided with one or several individual filaments extending in parallel. Since during the braid manufacturing process filaments are introduced into the process from bobbins, one or several individual filaments are fed from the respective bobbin simultaneously to the mandrel on which the braiding is produced. Each individual filament may consist of a single wire or of strands comprising several individual wires joined and preferably twisted together.

The individual wires may be of identical diameter and/or may have different diameters. The wires may also consist of different materials (nitinol, cobalt-chrome alloys, platinum alloys). Wires made of a radiopaque material, for example, enable the implant to be visible by radiographic methods.

As described hereinbefore, in regard to a stress-free arrangement of the individual filaments in the braiding it is essential for the implant surface to be structured so as to be as dense as possible. Since the flexibility of the braid must be maintained, a 100% coverage of the surface with filaments can at best be approached to some extent only, however. The surface coverage may also be reduced, however, and, depending on the relevant application, such a reduced surface coverage has also proved to be sufficient. Preferred is a surface covers age in the range of 30 to 80%, preferably between 35 and 70%.

To improve the surface coverage the braid may be coated with a film consisting, for example, of teflon, silicone or other biocompatible plastic material. To increase flexibility and expandability such a plastic film may be provided with slots which are of staggered arrangement, with the longitudinal direction of the slots extending along the peripheral line of the implant. Such a film may, for example, be produced by immersing the implant into a suitable liquid film medium (dispersion or solution) and subsequent provision of slots, for instance by means of laser equipment. By immersion the meshes may, for example, be filled fully or partly.

Alternatively, by immersion into a plastic dispersion or solution the individual filaments of the implant may be coated with such a plastic material and the filament cross section increased in this way. In this case, the mesh area remains open but the mesh size is significantly reduced.

The implant may be coated in a manner known per se. Suitable coating materials are, in particular, those described for stents, for example materials having antiproliferative, antiphlogistic, antithrombogeneous properties or hemocompatible characteristics conducive to ingrowth and/or preventing deposits. Preferred is a coating that promotes the ingrowth of the implant and the formation of neointima. It may be expedient to provide the implant externally with such a type of coating and inside use an agent that inhibits adherence, for example heparin or a derivative, ASS or oligosaccharides and chitin derivatives suitable for the purpose. Further suited in this context are layers of nanoparticles, for example ultrathin layers of polymeric $SiO_2$ reducing adherence.

As mentioned above, the combination of pusher wire with retaining element, tube-like sheathing, and implant is moved through a microcatheter. The diameter of the retaining element as well as the sheathing is sized so as to enable both to be easily guided together through a customary microcatheter. Accordingly, the present invention also relates to a device that comprises in addition to the implant, the tube-like sheathing, and the pusher wire also a microcatheter through which the additional components can be brought to the placement site. Moreover, the device may comprise a storage sleeve which for storage purposes can accommodate the implant and, as the case may be, the tube-like sheathing and pusher wire. For application and by using the pusher wire the implant is pushed out of the storage sleeve and into the microcatheter for which purpose a tapered transition piece is typically employed.

Aside from the inventive implant the invention also relates to a method for the manufacture of a tube-like sheathing that may be used in conjunction with a device as described hereinbefore. Such manufacture may be effected such that based on a sheathing of uniform outer diameter and uniform wall thickness in partial sections of the sheathing, in particular in the middle section, the outer diameter and the wall thickness are reduced by way of the removal of material. Alternatively, the sheathing may also be manufactured by attaching at least one partial section of the sheathing having a small outer diameter to partial sections of the sheathing having a large outer diameter. The attachment is advantageously made by an adhesive method.

The invention is explained in more detail by way of the following figures where

FIGS. 1a,b show a device with distal pusher wire tip;

FIGS. 2a,b show a device without distal pusher wire tip;

FIGS. 3a,b illustrate variants of joining the ends of filaments;

FIG. 5 depicts an embodiment of the invention wherein the outer diameter of the tube-like sheathing caries with step-like transitions;

FIG. 6 depicts another embodiment of the invention wherein the outer diameter of the tube-like sheathing varies with transitions of tapered configuration;

FIG. 7 illustrates another embodiment of the invention wherein the outer diameter of the tube-like sheathing varies with the sheathing comprising a plurality of individual components;

FIG. 8 shows another embodiment of the invention wherein the outer diameter of the tube-like sheathing is larger in the proximal section only;

Figure 1A:
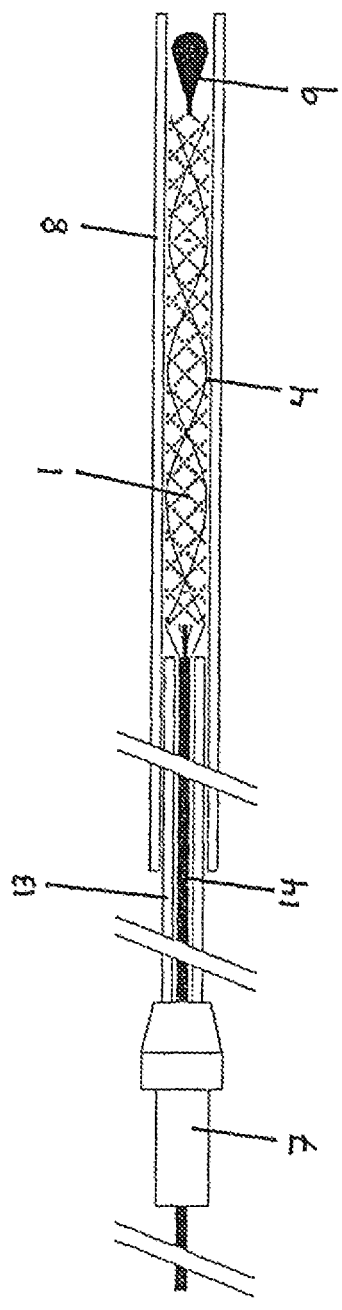

FIG. 1a illustrates the basic design of the inventive device in storage condition wherein the special features of the tube-like sheathing 13 are not visible in this representation. The device consists of an implant 1, a pusher wire 14, and a tube-like sheathing 13. The implant 1 comprises a braiding in which individual wires 4 of a radiopaque material are interlaced to ensure the implant 1 is visible during radiography. At the proximal end the implant 1 is coupled to the pusher wire 14 which is provided with a retaining element not shown here in detail. Extending from the proximal end of the implant 1 the connecting elements are secured in the retaining element, with the tube-like sheathing 13 preventing the connecting elements to become released from the retaining element. The pusher wire 14 extends through the implant 1 in distal direction and is provided with a pusher wire tip 9 located at the distal end. In the storage condition shown here the implant 1 is contained in a storage sleeve 8 out of which implant 1 is pushed into the microcatheter for application purposes. At the proximal end pusher wire 14 and tube-like sheathing 13 are held together by a torquer 7.

Figure 1B:
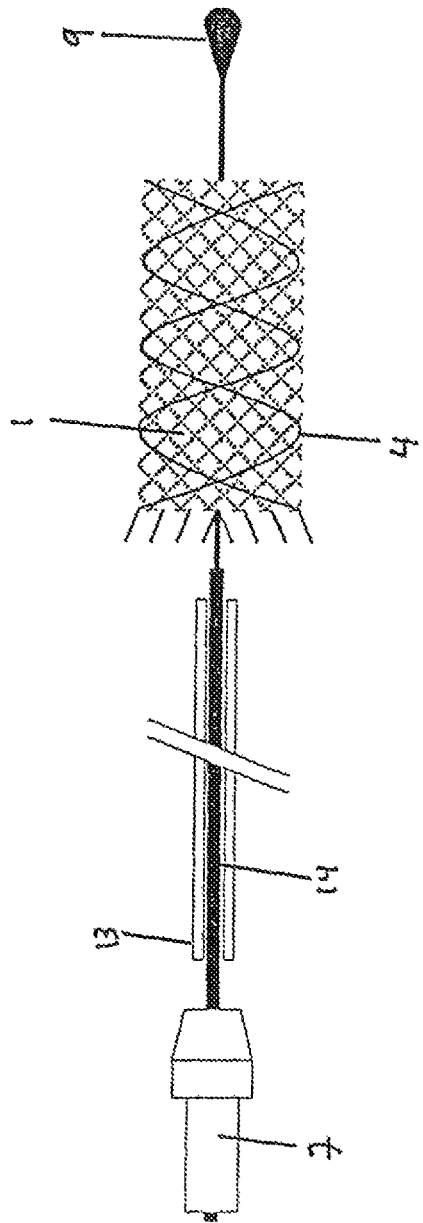

In FIG. 1b the implant 1 shown in FIG. 1a is illustrated in released state. The tube-like sheathing 13 has been retracted so that the connecting elements could disengage from the retaining element of pusher wire 14. The pusher wire tip 9 still extends through the implant 1 but may be withdrawn together with pusher wire 14 and sheathing 13.

Figure 2:
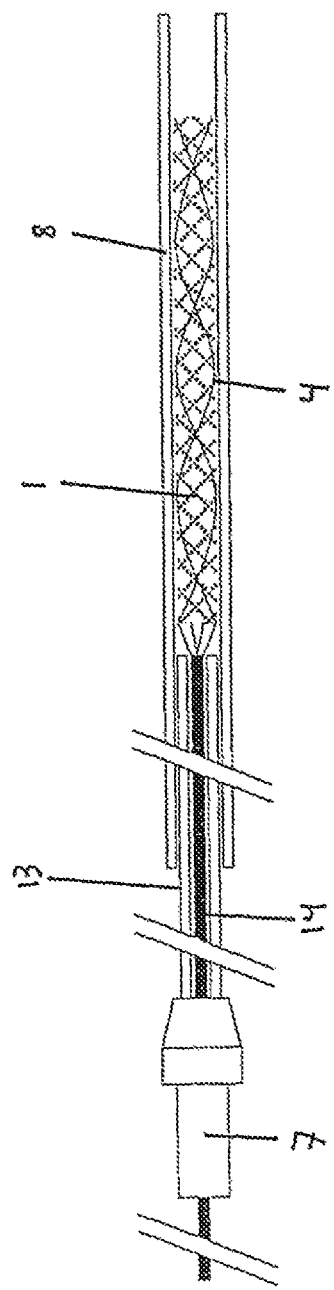
Figure 2:
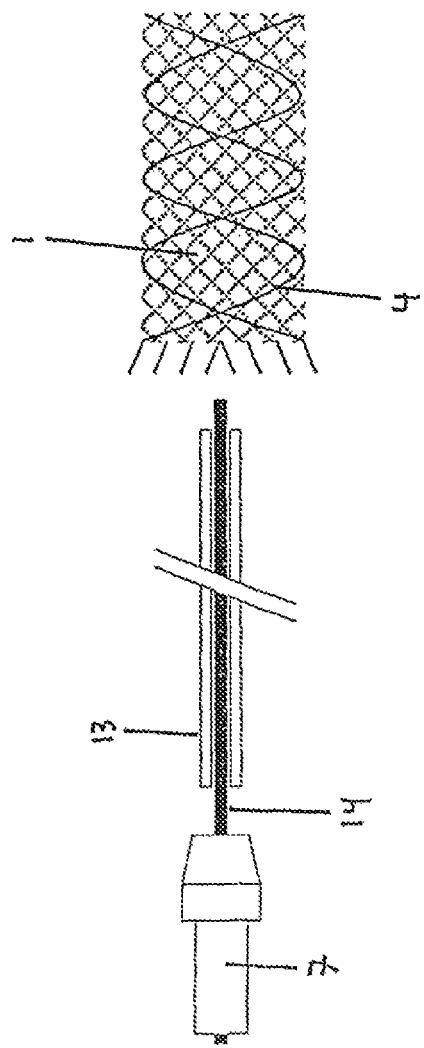

FIGS. 2a and 2b illustrate an embodiment of the invention that is basically identical with the one shown in FIGS. 1a and 1b, however, a distal pusher wire tip 9 has been omitted in this case.

Figure 3:
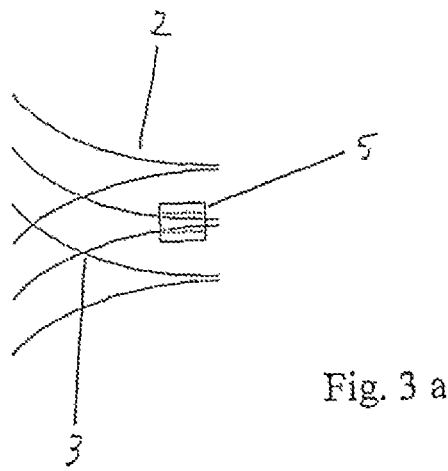
Figure 3:
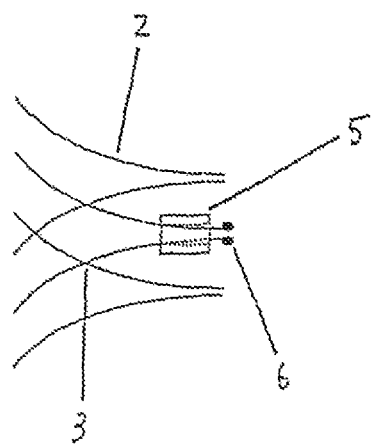

From FIG. 3a it can be seen how the ends of filaments 2 forming the braiding of implant 1 and intersecting at crossing points 3 are kept together at the proximal end by means of a sleeve 5. Sleeve 5 may be attached to the filaments by welding or crimping. Moreover, sleeve 5 may at the same time serve to visualize the implantation process provided said sleeve consists of a radiopaque material.

As is shown in FIG. 3b, the proximal filament ends are provided with atraumatic thickenings which serve as connecting elements 6. These may be formed out of the filament 2 or attached additionally. If thickening elements 6 are of sufficient diameter this alone will prevent sleeve 5 from sliding off the filament ends. However, sleeve 5 may of course also be retained/secured by crimping, welding, soldering, adhesive bonding or the like.

Figure 4:
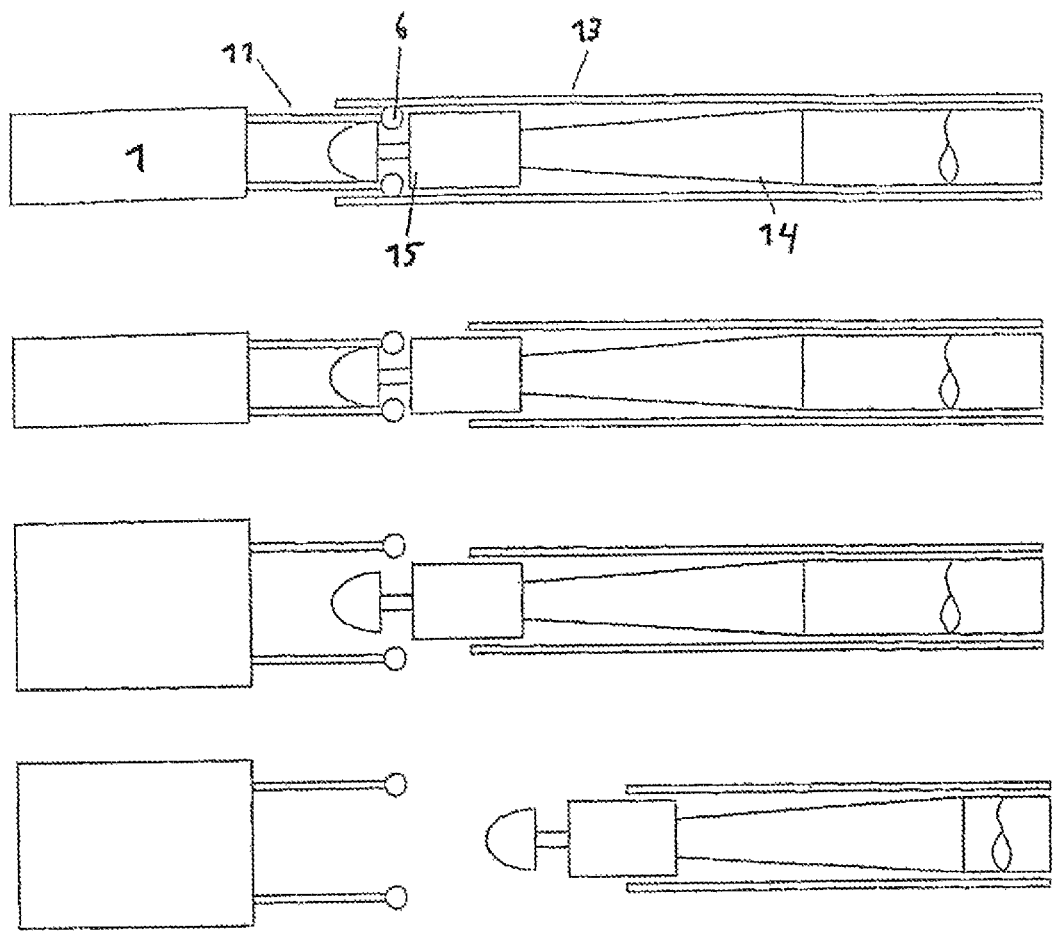
FIG. 4 shows the implant connection to and release from the retaining element.

FIG. 4 shows the fixation and detachment of implant 1 connected to pusher wire 14 via a retaining element 15. Retaining element 15 and pusher wire 14 are enclosed in a tube-like sheathing 13. Retaining element 15 is provided with cutouts in which the connecting elements 6 engage at the proximal end of implant 1. As long as the retaining element 15 encloses sheathing 13 the thickening elements 6 are prevented from exiting the retaining element 15. As soon as sheathing 13 is retracted the implant 1 is capable of expanding at the proximal end, with the connecting elements disengaging from the cutouts provided in retaining element 15. Subsequently, the pusher wire 14 to which distal end the retaining element 15 is attached can also be retracted.

In FIG. 5 an inventive embodiment of the device is depicted wherein for the sake of clarity the representation of the implant with its connecting elements has been omitted. At its distal end pusher wire 14 is provided with a pusher wire tip 9 as well as a retaining element 15 with cutouts 16 intended to accommodate the connecting elements originating from implant 1. A tube-like sheathing 13 encloses the retaining element 15 with connecting elements fitted in place and thus prevents the implant from being released.

According to the invention it is of significance that the outer diameter of the tube-like sheathing 13 varies. For this purpose, a distinction can roughly be made with respect to the sheathing 13 between a distal section 17 enclosing the retaining element 15, a middle section 18 which should be highly flexible and pliable, and a significantly longer proximal section 19. In the interest of bringing about sufficient pliability, the middle section 18 has an outer diameter which is smaller than that of the two other sections 17, 19.

Additionally, the diameter of the pusher wire 14 varies as well and in the proximal section 21 is larger than in the distal section 20. In this manner the flexibility of the pusher wire 14 and thus the entire device increases which is of significance when advancing it through the microcatheter in narrow blood vessels. The transition 22 between the proximal and distal sections of the pusher wire is tapered, i.e. gradual, in this case, whereas the transitions between the individual sections of the tube-like sheathing 13 are of step-like configuration. This is produced by plastic deformation.

In FIG. 6 a similar embodiment is shown wherein again the tube-like sheathing 13 is produced by plastic deformation. However, other than with the embodiment illustrated in FIG. 5 the transitions between the distal section 17 and middle section 18 and between the middle section 18 and proximal section 19 are tapered, that is they have a more gradual contour.

As per FIG. 7 the tube-like sheathing 13 is designed to comprise a plurality of parts and is thus composed of several sheathing segments bonded in an overlapping fashion. In this context, the sheathing segment forming the middle section 18 of sheathing 13 has a diameter lower than that of the sheathing segments of distal and proximal sections 17, 19. The individual sheathing segments may in particular be connected by adhesive bonding.

FIG. 8 illustrates an embodiment wherein the tube-like sheathing 13 is of one-piece configuration. From a sheathing having a uniform outer diameter and uniform wall thickness material is removed from the outside of the distal section 17 and the middle section 18 so that the outer diameter and the wall thickness are reduced in these sections. In this way, a tube-like sheathing 13 is obtained that has high distal flexibility and pliability.

Figure 9:
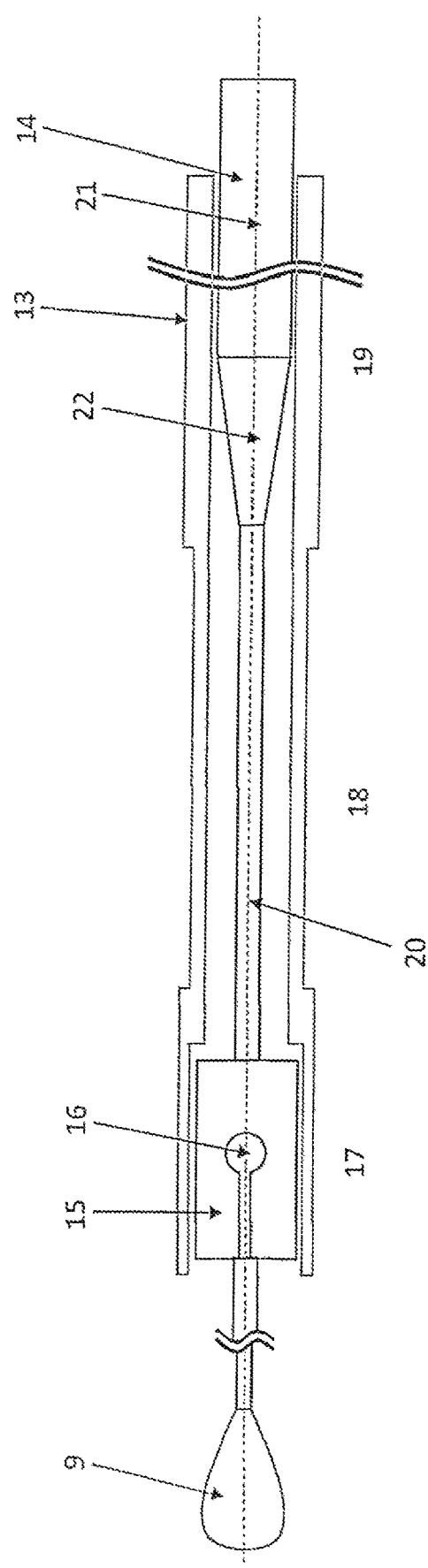
FIG. 9 depicts another embodiment of the invention wherein the outer diameter as well as the wall thickness of the tube-like sheathing varies.

FIG. 9 also shows a one-piece tube-like sheathing 13. However, other than is shown in FIG. 8 the distal section 17 has an outer diameter larger than that of middle section 18. This may prove especially expedient if the diameter of retaining element 15 is larger.

Although the transitions between the individual sections 17, 18, and 19 are shown in FIGS. 8 and 9 to have a step-like contour, rounded or chamfered transitions may of course also be provided, however. Likewise, several steps may be arranged at the transitions.

Figure 10:
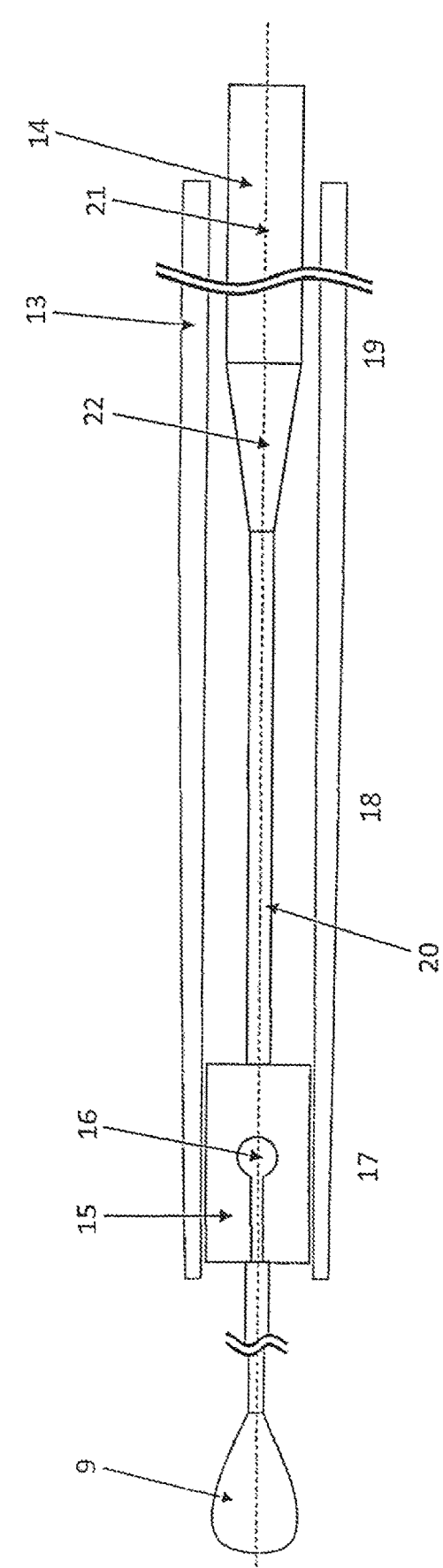
FIG. 10 shows another embodiment of the invention with a tapered tube-like sheathing.

In conclusion, FIG. 10 serves to illustrate an embodiment wherein the tube-like sheathing 13 is also of one-piece design but has an outer diameter that constantly reduces from the proximal section 19 to distal section 17 so that the sheathing 13 has a moderately conical shape. In the distal and middle sections 17, 18 material is removed from the outside of the sheathing 13 by means of turning or grinding methods. This also results in the pliability of sheathing 13 to increase distally.

The invention claimed is:

1. A device for introducing an implant into a blood vessel of a human body, said device comprising:
    an implant having a proximal end and a distal end,
    a pusher wire having a distal segment and a proximal segment, and
    a tube-like sheathing, wherein said tube-like sheathing further comprises a distal section, an adjacently arranged middle section proximal to said distal section, and a proximal section proximal to said middle section, said distal section having a first outer diameter, said middle section having a second outer diameter smaller than the first outer diameter, said proximal section having a third outer diameter larger than the second outer diameter, said distal section having a first inner diameter, said middle section having a second inner diameter, and said proximal section having a third inner diameter, the second and third inner diameter being uniform,
    wherein the distal segment of the pusher wire is disposed in the middle section of the tube-like sheathing, and terminates proximally near a proximal end of the middle section, and the proximal segment of the pusher wire having a larger diameter than the distal segment of the pusher wire is disposed within the proximal section of the tube-like sheathing, and terminates distally near a distal end of the proximal section of the tube-like sheathing,
    wherein the implant is capable of being deformed inside a microcatheter in a manner that allows it to assume a shape of reduced diameter and, after omission of such external constraint exerted by the microcatheter, expand at a placement site within the blood vessel and adapt to the blood vessel, and
    wherein the implant is provided at the proximal end with connection elements attaching it to a retaining element by means of which the implant is coupled to the pusher wire, and wherein the retaining element is provided with peripheral cutouts into which the connection elements are fitted, with the tube-like sheathing being disposed over the retaining element with fitted connection elements such that the connection elements are secured within the cutouts of the retaining element and the implant configured to be released by the retraction of the tube-like sheathing in a proximal direction.

2. A device according to claim 1, wherein the proximal section has a wall thickness greater than a wall thickness of the middle section.

3. A device according to claim 1, wherein the tube-like sheathing is of one-piece design and obtained in such a way that based on a sheathing of uniform outer diameter and constant wall thickness, said outer diameter and the wall thickness are reduced by removal of material in the middle section.

4. A device according to claim 1, wherein the pusher wire has a diameter that varies over its length.

5. A device according to claim 1, wherein a distal end of the pusher wire extends further distally than the distal end of the implant in a state fixed in the retaining element.

6. A device according to claim 1, wherein the implant has a wall composed of individual filaments intersecting with one another and forming a tubular braiding.

7. A device according to claim 1, wherein the distal section has a wall thickness greater than a wall thickness of the middle section.

8. A device for introducing an implant into a blood vessel of a human body, said device comprising:
    an implant having a proximal end and a distal end,
    a pusher wire having a distal segment and a proximal segment, and
    a tube-like sheathing, wherein said tube-like sheathing further comprises a distal section, an adjacently arranged middle section proximal to said distal section, and a proximal section proximal to said middle section, said distal section having a first outer diameter, said middle section having a second outer diameter smaller than the first outer diameter, said proximal section having a third outer diameter larger than the second outer diameter, said distal section having a first inner diameter, said middle section having a second inner diameter, and said proximal section having a third inner diameter, the second and third inner diameter being uniform,
    wherein the distal segment of the pusher wire is disposed in the middle section of the tube-like sheathing, and terminates proximally near a proximal end of the middle section, and the proximal segment of the pusher wire having a larger diameter than the distal segment of the pusher wire is disposed within the proximal section of the tube-like sheathing, and terminates distally near a distal end of the proximal section of the tube-like sheathing, and
    the proximal section of the tube-like sheathing, and the proximal segment of the pusher wire, comprise at least about half the length of the tube-like sheathing,
    wherein the implant is capable of being deformed inside a microcatheter in a manner that allows it to assume a shape of reduced diameter and, after omission of such external constraint exerted by the microcatheter, expand at a placement site within the blood vessel and adapt to the blood vessel, and
    wherein the implant is provided at the proximal end with connection elements attaching it to a retaining element by means of which the implant is coupled to the pusher wire, and wherein the retaining element is provided with peripheral cutouts into which the connection elements are fitted, with the tube-like sheathing being disposed over the retaining element with fitted connection elements such that the connection elements are secured within the cutouts of the retaining element and the implant configured to be released by the retraction of the tube-like sheathing in a proximal direction.

9. A device for introducing an implant into a blood vessel of a human body, said device comprising:

a tube-like sheathing, wherein said tube-like sheathing further comprises a distal section, an adjacently arranged middle section proximal to said distal section, and a proximal section proximal to said middle section, said distal section having a first outer diameter, said middle section having a second outer diameter smaller than the first outer diameter, said proximal section having a third outer diameter larger than the second outer diameter, said distal section having a first inner diameter, said middle section having a second inner diameter, and said proximal section having a third inner diameter, the second and third inner diameter being uniform, an implant disposed within the distal section of the tube-like sheathing, said implant having a proximal end and a distal end, wherein the implant is capable of being deformed inside a microcatheter in a manner that allows it to assume a shape of reduced diameter and, after omission of such external constraint exerted by the microcatheter, expand at a placement site within the blood vessel and adapt to the blood vessel, a pusher wire having a distal segment and a proximal segment, wherein the distal segment of the pusher wire is disposed in the middle section of the tube-like sheathing, and terminates proximally near a proximal end of the middle section, and the proximal segment of the pusher wire having a larger diameter than the distal segment of the pusher wire is disposed within the proximal section of the tube-like sheathing, and terminates distally near a distal end of the proximal section of the tube-like sheathing, and wherein the implant is provided at the proximal end with connection elements attaching it to a retaining element by means of which the implant is coupled to the pusher wire, and wherein the retaining element is provided with peripheral cutouts into which the connection elements are fitted, with the tube-like sheathing being disposed over the retaining element with fitted connection elements such that the connection elements are secured within the cutouts of the retaining element and the implant configured to be released by the retraction of the tube-like sheathing in a proximal direction.

\* \* \* \* \*